(12) United States Patent
Landherr et al.

(10) Patent No.: US 8,728,023 B2
(45) Date of Patent: May 20, 2014

(54) APPARATUS AND METHODS FOR EARLY STAGE PERITONITIS DETECTION INCLUDING SELF-CLEANING EFFLUENT CHAMBER

(75) Inventors: Frank J. Landherr, Cary, IL (US); Jay M. Lan, Thousand Oaks, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1364 days.

(21) Appl. No.: 12/020,192

(22) Filed: Jan. 25, 2008

(65) Prior Publication Data

US 2008/0183127 A1    Jul. 31, 2008

Related U.S. Application Data

(63) Continuation-in-part of application No. 11/880,656, filed on Jul. 23, 2007.

(60) Provisional application No. 60/833,763, filed on Jul. 27, 2006.

(51) Int. Cl.
*G06F 19/00* (2011.01)
*A61M 1/00* (2006.01)
*B01D 61/00* (2006.01)

(52) U.S. Cl.
USPC .......... 604/29; 604/19; 604/27; 702/19; 210/645; 600/309

(58) Field of Classification Search
None
See application file for complete search history.

(56) References Cited

U.S. PATENT DOCUMENTS

| | | | |
|---|---|---|---|
| 4,279,509 A * | 7/1981 | Daffern | 356/246 |
| 5,007,732 A * | 4/1991 | Ohki et al. | 356/73 |
| 5,025,523 A | 6/1991 | Zappa et al. | |
| 5,304,173 A | 4/1994 | Kittrell et al. | |
| 5,383,199 A | 1/1995 | Laudenslager et al. | |
| 5,690,813 A | 11/1997 | Coale | |
| 6,067,157 A | 5/2000 | Altendorf | |
| 6,228,047 B1 | 5/2001 | Dadson et al. | |
| 2003/0044853 A1 * | 3/2003 | Socks et al. | 435/7.9 |
| 2003/0059370 A1 | 3/2003 | Quijano et al. | |
| 2005/0139515 A1 | 6/2005 | Gu et al. | |
| 2005/0213425 A1 | 9/2005 | Wang et al. | |
| 2006/0154642 A1 | 7/2006 | Scannell | |
| 2007/0020341 A1 | 1/2007 | Miyata | |
| 2008/0015487 A1 | 1/2008 | Szamosfalvi et al. | |
| 2008/0045884 A1 | 2/2008 | Landherr et al. | |
| 2008/0183126 A1 | 7/2008 | Landherr et al. | |
| 2008/0183127 A1 | 7/2008 | Landherr et al. | |

FOREIGN PATENT DOCUMENTS

| | | |
|---|---|---|
| JP | 08-098882 A | 4/1996 |
| JP | 08-107890 A | 4/1996 |
| JP | 8089571 | 4/1996 |
| JP | 09-210995 A | 8/1997 |
| JP | 09-239023 * | 9/1997 |
| JP | 09-239023 A | 9/1997 |
| JP | 2001-509888 A | 7/2001 |
| JP | 2001-511400 A | 8/2001 |
| JP | 2003-501155 A | 1/2003 |
| JP | 2006-149938 A | 6/2006 |
| JP | 2011-510324 A | 3/2011 |
| WO | 01/17422 A1 | 3/2001 |
| WO | 2004/093669 A1 | 11/2004 |

OTHER PUBLICATIONS

Zinn et al (Methods in Enzymology, vol. 310, p. 224-232, 1999).*
Ellis et al. (Analyst, 2006, 131, 875-885).*
Keane et al. (Peritoneal Dialysis International, vol. 16, pp. 557-573, 1996).*
International Search Report, International Application No. PCT/US08/52056, Mailed Aug. 1, 2008.
International Search Report, International Application No. PCT/US08/52062, Mailed Jul. 25, 2008.
Sharma. Evaluation of fiberoptic-based systems for measurement of optical properties in highly attenuating turbid media. Biomed Eng Online. Aug. 23, 2006, 5(49):1-14.
Ellis et al., Metabolic fingerprinting in disease diagnosis: biomedical applications of infrared and Raman spectroscopy. Analyst. Aug. 2006;131(8):875-85. Epub Apr. 25, 2006.

(Continued)

*Primary Examiner* — Lori A Clow
(74) *Attorney, Agent, or Firm* — Nutter McClennen & Fish LLP; David J. Powsner (57) ABSTRACT

The invention provides, inter alia, automated medical methods and apparatus that test PD effluent in a flow path (e.g., with an APD system or CAPD setup) to detect, for example, the onset of peritonitis, based on optical characteristics of the effluent resolved at cellular scales of distance. For example, according to one aspect of the invention, an APD machine includes, in an effluent flow path, apparatus for early stage peritonitis detection comprising an illumination source and a detector. The source is arranged to illuminate peritoneal effluent in a chamber that forms part of the flow path, and the detector is arranged to detect illuminant scattered by the effluent. The detector detects that reflected or scattered illuminant at a cellular scale of resolution, e.g., on a scale such that separate cellular-sized biological (or other) components in the effluent can be distinguished from one another based on scattering events detected by the detector. According to aspects of the invention, the chamber can utilize a deflector to effect turbulent flow for purposes of cleaning biological and other materials from the chamber walls.

17 Claims, 8 Drawing Sheets

(56) References Cited

OTHER PUBLICATIONS

Keane WF, Alexander SR, Bailie GR, Boeschoten E, Gokal R, Golper TA, Holmes CJ, Huang CC, Kawaguchi Y, Piraino B, Riella M, Schaefer F, Vas S. Peritoneal dialysis-related peritonitis treatment recommendations: 1996 update. Perit Dial Int. Nov.-Dec. 1996;16(6):557-73.

Japanese Office Action issued Feb. 24, 2012 for Application No. 2010-544287.

Zinn et al., Laminar flow chamber for continuous monitoring of biofilm formation and succession. Methods Enzymol. 1999;310:224-32.

Chow et al., Predictive value of dialysate cell counts in peritonitis complicating peritoneal dialysis. Clin J Am Soc Nephrol. 2006;1:768-773.

Baena et al., Raman spectroscopy in chemical bioanalysis. Curr Opin Chem Biol. Oct. 2004;8(5):534-9.

Leary et al., Laser flow cytometric light scatter and fluorescence pulse width and pulse rise-time sizing of mammalian cells. J Histochem Cytochem. Jan. 1979;27(1):315-20.

Penders et al., Automated flow cytometry analysis of peritoneal dialysis fluid. Nephrol Dial Transplant. 2004;19 (2):463-8.

Terstappen et al., Four-parameter white blood cell differential counting based on light scattering measurements. Cytometry. 1988;9:39-43.

Japanese Office Action issued Oct. 19, 2012 for Application No. 2010-544288 (7 Pages).

[No Author Listed] The Raman Effect published Dec. 15, 1998 by the American Chemical Society for short overview of Raman Spectroscopy.

Canadian Office Action for Application No. 2594634, issued Oct. 22, 2013 ( 4 pages).

\* cited by examiner

APPARATUS AND METHODS FOR EARLY STAGE PERITONITIS DETECTION INCLUDING SELF-CLEANING EFFLUENT CHAMBER

This application is a continuation in part of U.S. patent application Ser. No. 11/880,656, filed Jul. 23, 2007, entitled "Early Stage Peritonitis Detection Apparatus and Methods," which claims the benefit of U.S. Provisional Patent Application Ser. No. 60/833,763, filed Jul. 27, 2006, entitled "Early Stage Peritonitis Detection Apparatus and Methods," the teachings of which are incorporated herein by reference.

BACKGROUND OF THE INVENTION

The invention relates to apparatus and methods for medical diagnostic testing. It has application, inter alia, in detecting the onsite of peritonitis, for example, during continuous ambulatory peritoneal dialysis (CAPD) and automated peritoneal dialysis (APD) procedures.

Peritoneal dialysis (PD) is a medical procedure for removing toxins from the blood that takes advantage of the semipermeable membrane surrounding the walls of the abdomen or peritoneal cavity. During a PD procedure, a solution is introduced into the patient's abdomen, where it remains for up to several hours, removing blood toxins via osmotic transfer through that membrane. At completion of the procedure, the solution is drained from the body along with the toxins. CAPD is the manual form of this procedure, requiring that the patient manually drain fresh PD solution into, and spent PD solution out from, the peritoneum. In APD, the entire procedure is handled by automated equipment.

Peritonitis is a common complication of both CAPD and APD. Often caused by introduction of bacteria (e.g., from the tubing, connectors and other apparatus that make up the PD transfer set) to the peritoneum during dialysis, this swelling of the peritoneum can cause vomiting, abdominal tenderness and a host of other symptoms. Although responsive to antibiotics, peritonitis can end a patient's ability to stay on APD and CAPD therapies. In extreme cases, it can be be fatal.

Standard tests for peritonitis, usually conducted on occurrence of acute clinical symptoms, include the Gram stain procedure, performing a cell count on the peritoneal fluid, culturing that fluid, and/or performing a blood culture. Largely, these tests can only be done in the lab, after a patient has presented with symptoms. By that time, the peritonitis may well have set in, resulting in undue patient distress and potentially necessitating more extensive treatment.

More recently, reagent test strips have become available, making it possible for physicians or patient's themselves to perform more immediate diagnosis. However, test strips have a limited time window of utility and have generally not been successful in early stage detection.

CAPD and APD patients are typically counseled to maintain a keen eye for another symptom of peritonitis: a turbid or cloudy effluent bag. This can be late-developing, unfortunately, and is further compounded if the PD solution remains in the body for a long period before expulsion (as is the case, for example, during daytime dwells of APD patients). Detection of turbid effluent is further complicated in APD equipment with long drain lines, since patients may only see the effluent lines and not the effluent bag (where the turbidity is more readily apparent). Moreover, patients who are blind or have poor eyesight must rely on friends, family and/or caregivers to inspect the spent PD fluid for turbidity.

The prior art suggests that such cloudiness might be detected automatically, e.g., within APD equipment, by detecting the overall amount of non-coherent, polychromatic light that passes through a vessel of PD effluent by use of a source of such light positioned on one side of the vessel and a detector positioned at an opposing side. Implementations of this technique have generally not proven reliable because of poor signal-to-noise.

An object of the invention is to provide improved methods and apparatus for medical diagnosis, testing and/or treatment in the home or lab.

A further object of the invention is to provide improved methods and apparatus for PD therapy.

A still further object of the invention is to provide improved methods and apparatus for detecting the onset of peritonitis, e.g., in connection with peritoneal dialysis.

Yet a still further object of the invention is to provide such methods and apparatus as can be implemented at reasonable cost, yet, produce efficacious results.

SUMMARY OF THE INVENTION

The foregoing are among the objects attained by the invention which provides, in one aspect, automated medical testing methods and apparatus that detect the onset of peritonitis from optical characteristics of PD effluent resolved at cellular scales in the flow path.

For example, according to one aspect of the invention, an APD machine includes, in an effluent flow path, apparatus for early stage peritonitis detection comprising an illumination source and a detector. The source is arranged to illuminate peritoneal effluent in a chamber that forms part of the flow path, and the detector is arranged to detect illuminant scattered by the effluent. The detector detects that scattered illuminant at a cellular scale of resolution, e.g., on a scale such that separate cellular-sized biological (or other) components in the effluent can be distinguished from one another based on scattering events detected by the detector.

Related aspects of the invention provide apparatus as described above in which the detector is arranged such that separate white blood cells (WBCs) in the effluent can be distinguished from one another based on reflection and scattering (collectively, "scattering") of illuminant. Apparatus with a detector so arranged can, by way of example, count such WBCs from scattering and can, further, signal the onset of peritonitis if those counts change over time and/or vary from a baseline.

Further related aspects of the invention provide apparatus as described above in which the detector is arranged such that cellular-sized biological (or other) components of different types in the effluent can be distinguished based on illuminant scattered by them. Related aspects of the invention provide such apparatus in which the detector is so arranged as to permit WBCs in the effluent to be distinguished based on scattering from red blood cells (RBCs), fibrin and/or other components.

Other aspects of the invention provide apparatus as described above which signal the onset of peritonitis based on variance, e.g., over time and/or from a baseline, in counts of selected biological components in the effluent. Related aspects of the invention provide such apparatus as compute a trend of variance of those counts, e.g., with respect to WBCs in the effluent. Further related aspects of the invention provide such apparatus which compute that trend as a slope of a curve of those counts with respect to time and that signals the onset of peritonitis when that slope exceeds a selected amount.

Other related aspects of the invention provide such apparatus in which the detector counts scattering events—i.e., events in which illuminant is reflected and scattered from the effluent to the detector—based on intensity and/or location of the scattering event. In one such aspect of the invention, the detector comprises a pin diode that is configured to count scattering events, e.g., based on the intensity of illuminant detected from the effluent. An apparatus according to this aspect of the invention can, for example, signal the onset of peritonitis when the number of counts of a certain intensity (or range of intensities, e.g., which are based on cell size) varies, e.g., from a baseline and/or among drains of spent PD solution from the patient, and/or when a trend of that variance over time exceeds a selected amount.

In other such aspects, the detector comprises a charge-coupled device (CCD) that is arranged to image the chamber—that is, to record scattering events based on both location and (cumulative) intensity. Further related aspects of the invention provide such apparatus in which the detector generates a histogram of one or more such images, counting scattering events (e.g., based on intensity). Still further related aspects of the invention provide such apparatus which generates a histogram from multiple images taken, for example, during a drain of spent PD solution from the patient. As above, apparatus according to these aspects of the invention can, for example, signal the onset of peritonitis when the number of counts of a certain intensity (or range of intensities) varies over time, e.g., from a baseline and/or among successive drains of PD effluent from the patient.

Other related aspects of the invention provide such apparatus which the histograms are performed only with respect to selected scattering events recorded in the images, e.g., scattering events of selected intensities and/or lengths. Apparatus accord to these aspects of the invention can, for example, signal the onset of peritonitis when the number of counts from scattering events likely caused by WBCs (and not, for example, RBCs or fibrin) vary over time from a baseline and/or among successive drains of PD effluent from the patient.

Further aspects of the invention provide such apparatus in which the illumination source is a laser diode (or other source of coherent illuminant).

Related aspects of the invention provide such apparatus in which the detector is arranged to detect side-scattering events, e.g., events detectable within a field of view perpendicular to a ray of illuminant sourced by the laser diode.

Further related aspects of the invention provide such apparatus in which illuminant sourced by the laser diode comprises a beam disposed—and, specifically, for example, centered—within a portion of the flow path from which scattering events are counted by the detector.

Still further related aspects of the invention provide such apparatus in which illuminant sourced by the laser has a beam width selected based on size characteristics of the biological (or other) components from which scattering events are to be counted. Further related aspects of the invention provide such methods in which the beam width has a diameter of about 1.5 times a size of components, e.g., WBCs. Yet still other aspects of the invention provide such apparatus in which the beam width has any of a circular and gaussian cross-section, or other beam size and/or shape.

Further aspects of the invention provide such apparatus in which the detector comprises a lens arranged to resolve illuminant scattered from components of the effluent at a cellular scale of distances. Related aspects of the invention provide such apparatus in which the lens is arranged to provide a depth of field encompassing a substantive portion of the flow path within the detector field of view, e.g., a depth of field that encompasses a flow chamber from which scattering events are detected.

Further aspects of the invention provide apparatus as described above in which the aforementioned chamber induces lamellar flow in the effluent. Such a chamber can comprise, for example, an optically clear portion having a central portion with inner walls defining a generally cuboid or rectangular parallelepiped region.

The central portion can, according to related aspects of the invention, be coupled with a flow inlet port via a portion of the chamber having inner walls generally defining a pyramidal frustum. Likewise, the central portion can, according to still further related aspects of the invention, be coupled with a flow outlet port via a portion of the chamber having inner walls that also generally define a pyramidal frustum.

Still further aspects of the invention provide apparatus as described above wherein the chamber comprises a deflector disposed in the flow path. The deflector can increase turbulence of effluent flowing in the chamber, increasing the Reynold's number of the fluid, e.g., to a value of about 100 or greater and, more preferably, of about 250 or greater. In these and other aspects of the invention, turbulence introduced into the flow as a result of the deflector facilitates cleaning its inner walls—particularly, for example, removing from them white blood cells, red blood cells and other components of the effluent.

Other aspects of the invention provide automated medical testing methods and apparatus paralleling those described above that detect the onset of peritonitis and other conditions by testing peritoneal fluid in vivo, i.e., in the patient's peritoneum. According to one aspect of the invention, such an apparatus includes an illumination source and a detector as described above, both disposed external to the patient. A first fiber optic bundle carries illuminant from the source into the peritoneum. A second fiber optic bundle carries illuminant scattered by peritoneal fluid in the peritoneum to the detector.

Related aspects of the invention provide apparatus as described above, wherein distal ends of the first and second fiber optic bundles are configured so that the latter detects and transmits to the detector reflected and/or scattered (collectively, "scattered") illuminant at a cellular scale of resolution, e.g., on a scale such that separate cellular-sized biological (or other) components in the peritoneal fluid can be distinguished from one another.

In other related aspects of the invention, one or more of the fiber optic bundles are routed from the apparatus to the patient's peritoneum via a catheter. This can be, for example, a catheter that forms part of an APD machine, CAPD system, or other equipment with which the apparatus is used. In related aspects, the bundles can enter the catheter via a y-connector, direct insertion into the wall of the catheter, or otherwise.

In still other related aspects of the invention, illuminant generated by the source (e.g., a laser diode) is shaped by lens or columinator for transfer via the first optic bundle to the peritoneum. Likewise, a further lens or columinator can be provided at the distal end of the first bundle to shape the illuminant in the peritoneum, e.g., to achieve a gaussian or circular cross-section. In further related aspects of the invention, a beam of illuminant emanating from the distal end of the first bundle can be aimed to pass through peritoneum so as to illuminate peritoneal fluid therein for purposes of evoking scattering from biological (and other) components in that fluid.

In yet other related aspects of the invention, the second fiber optic bundle is arranged to capture—and, thereby, to transmit to the detector—illuminant side-scattered by peritoneal fluid within the peritoneum. In related aspects of the invention, that bundle is arranged to capture and transmit to the detector illuminant back-scattered, forward-scattered, and/or side-scattered in the peritoneum.

Other aspects of the invention provide apparatus as described above which signal the onset of peritonitis or other conditions via a remotely disposed interface. In these regards, the apparatus and the remotely disposed interface can be coupled for communication via a wireless link, such as a Bluetooth® connection. Other aspects provide for such coupling via a wired link or a combination of wired and wireless links.

The remote interface can, according to still other aspects of the invention, receive signaling from the aforementioned apparatus and display it, e.g., via liquid crystal display, light-emitting diodes, or other indicators, to the patient, health care provider, or others. Furthermore, the remote interface can control the apparatus, e.g., in response to input from the patient, health care provider or others. This can include activating the apparatus, instigating coupling/decoupling of the interface and apparatus, specifying operational modes for the apparatus or otherwise.

In still other aspects of the invention, the remote interface is sized and configured to be slipped onto/into a pocket or "worn" by the patient, health care provider, or otherwise.

Still other aspects of the invention provide apparatus as described above that detects and measures an index of refraction of peritoneal fluid in the patient's peritoneum.

Other aspects of the invention provide apparatus as described above for use in connection with CAPD procedures.

Still other aspects of the invention provide such apparatus for use in detecting the onset of peritonitis in fluid flows established independent of APD and/or CAPD equipment in which the PD fluid is collected. Such apparatus has application, for example, in testing bags (or other collections) of spent PD effluent, e.g., as they are being emptied for disposal or for further testing.

Yet still other aspects of the invention provide PD kits that include, in addition to conventional components (such as tubing, clamps, sterilization wipes, and so forth), a test apparatus as described above.

Still yet other aspects of the invention provide methods of testing PD effluent for the onset of peritonitis paralleling the operations described above.

Yet still other aspects of the invention provide apparatus as described above for in vivo testing of bodily fluids including and other than peritoneal fluid.

Yet still other aspects of the invention provide apparatus and methods as described above for use in detecting characteristics of dialysate and other fluids contained in and/or from bodily organs and cavities in vitro, in vivo and otherwise, including characteristics such as indexes of refraction, the presence of blood (RBCs), bubbles and other undesirable byproducts of CAPD, APD, and so forth. A related aspect of the invention is to provide such apparatus and methods for use in hemodialysis and other medical procedures

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Figure 1A:
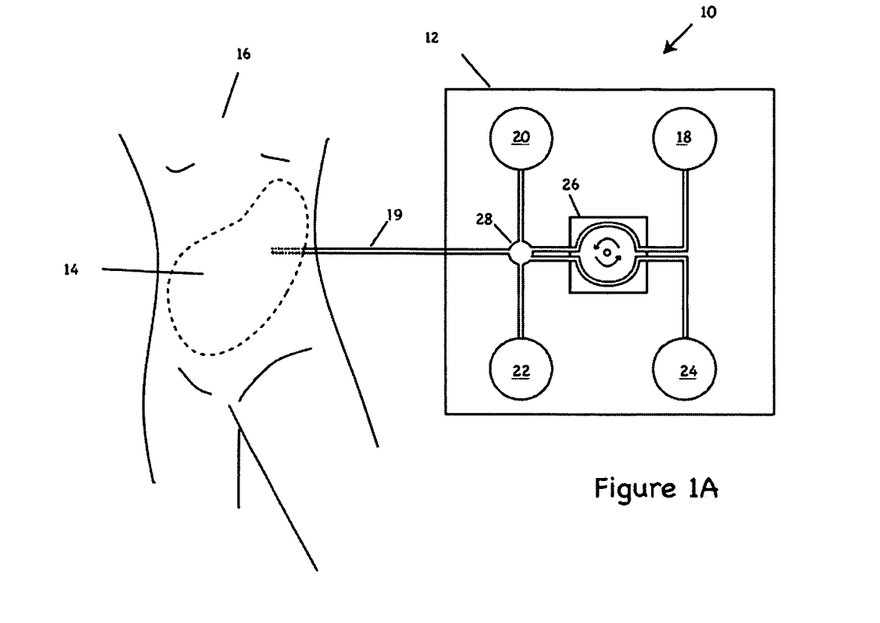
FIGS. 1A-1E depict an automated peritoneal dialysis (APD) treatment system according to one practice of the invention and of the type with which the invention can be practiced.

FIG. 1A depicts an automated peritoneal dialysis (APD) treatment system 10 according to one practice of the invention and of the type with which the invention can be practiced. The system 10 includes a cycler 12 or other apparatus to facilitate introducing fresh peritoneal dialysis (PD) solution into, and removing spent PD solution from, the peritoneum 14 of a patient 16.

The system 10 includes a PD solution supply chamber 18, a heating chamber 20, a weigh chamber 22, and a disposal chamber 24, all constructed an operated in the conventional manner known in the art (albeit as adapted for inclusion of PD effluent test apparatus as discussed elsewhere herein). Thus, PD supply chamber 18 holds a supply of fresh PD solution for delivery to the patient 16; heating chamber 20 brings the fresh PD solution to an appropriate temperature for delivery to the peritoneum; weigh chamber 22 hold spent PD solution expelled from the peritoneum, e.g., for weighing; and, disposal chamber 24 holds spent PD solution for disposal.

Figure 1B:
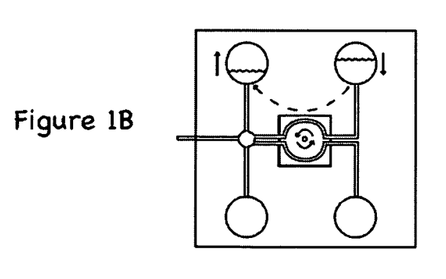
Figure 1C:
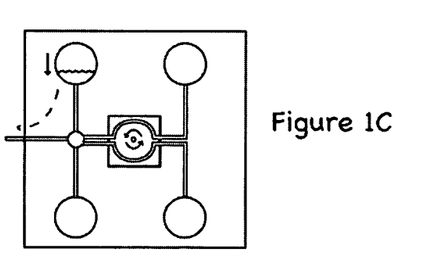

Pump 26 operates under control of a micro-controller (not shown) to move solution between the chambers 18-24 in the conventional manner, e.g., as illustrated in FIGS. 1B-1E. Thus, for example, as shown in FIG. 1B, pump 26 moves fresh PD solution from supply chamber 18 to heating chamber 20 so that the latter can bring that solution to temperature, prior to its introduction into the patient's peritoneum 14 via catheter 19. Once the desired temperature is achieved and treatment is to begin, the pump 26 opens a valve 28, allowing the heated, fresh PD solution to flow via gravity-assist into the peritoneum 14. See, FIG. 1C.

Figure 1D:
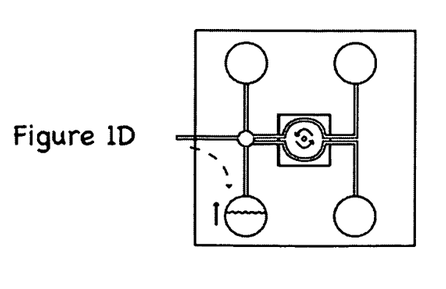
Figure 1E:
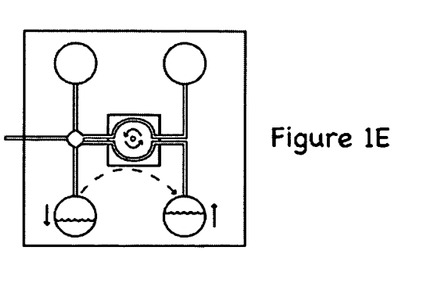

Per FIG. 1D, once the PD has dwelled for the desired period of time in the peritoneum 14, pump 26 opens valve 28 so that the spent PD solution can flow into chamber 22 for weighing (e.g., to insure that sufficient solution has be removed from the peritoneum 14), as per convention in the art. Pump 26 then moves the spent effluent from the weigh chamber 22 to the disposal chamber 24 for collection prior to disposal by the patient, health care worker, or otherwise. See, FIG. 1D.

The conventional aspects of system 10 shown and described here are merely by way of example. It will be appreciated that apparatus for testing PD effluent (as discussed elsewhere herein) may be used in connection with APD equipment of other configurations and modes of operation than those shown in FIGS. 1A-1E and described above.

Figure 2A:
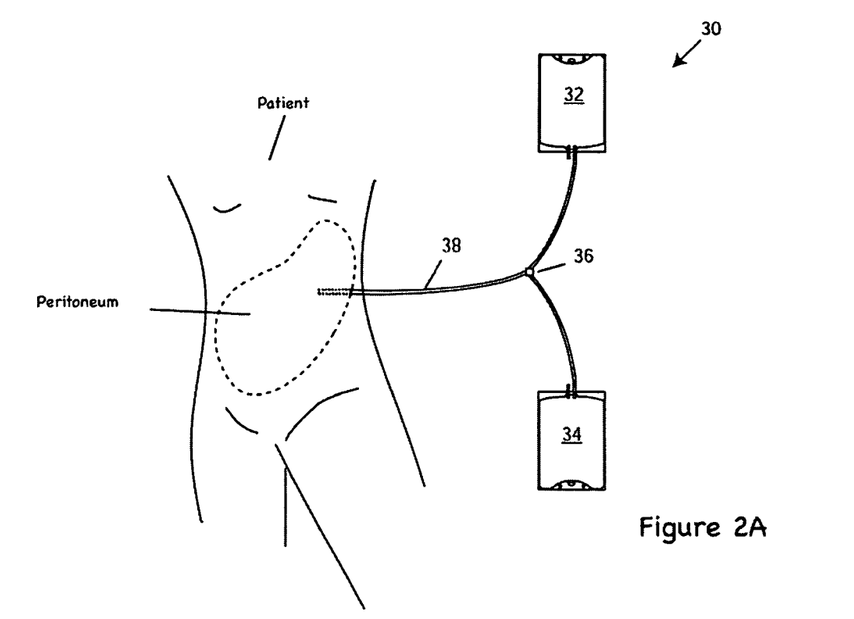
FIGS. 2A-2C depict a continuous ambulatory peritoneal dialysis (CAPD) treatment system according to one practice of the invention and of the type with which the invention can be practiced.
Figure 2B:
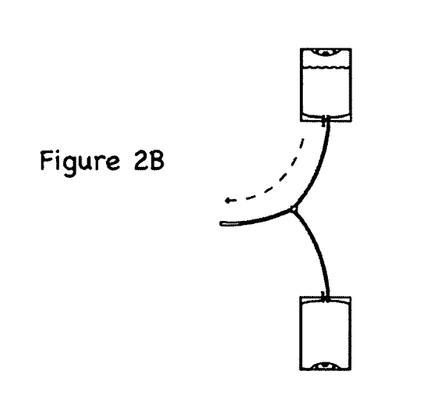
Figure 2C:
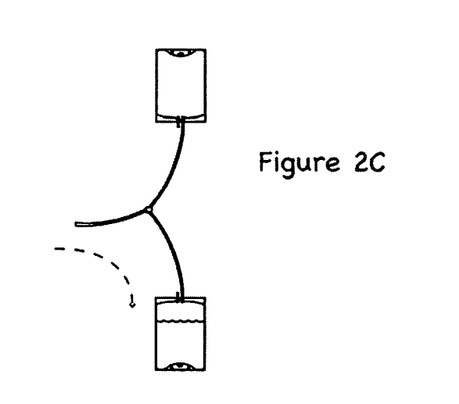

FIG. 2A depicts a continuous peritoneal dialysis (CAPD) treatment system 30 according to one practice of the invention and of the type with which the invention can be practiced. The system 30 includes a fresh PD solution supply bag 32, a spent PD solution bag 34, and a y-connector 36 for coupling those bags to peritoneal transfer set 38. The system 30 is constructed and operated in the conventional manner known in the art (albeit as adapted for inclusion of PD effluent test apparatus as discussed elsewhere herein). Thus, for example, the patient connects bags 32, 34 to the y-connector 36, as shown in FIG. 2B, for a brief sterilizing flush of the connector 36. Then, as further shown in that drawing, the patient configures the connector 36 to permit fresh PD solution to flow, under gravity assist, from bag 32 into the peritoneum. Once the PD solution has dwelled for the desired period, the patient reconfigures the connector 36 to permit the spent PD solution to drain to bag 34 for disposal. See, FIG. 2C.

The conventional aspects of system 30 shown and described here are merely by way of example. It will be appreciated that apparatus for testing PD effluent (as discussed elsewhere herein) may be used in connection with CAPD equipment of other configurations (e.g., with straight transfer tubing sets) and modes of operation than those shown in FIGS. 2A-2C and described above.

Figures 3A, 3B:
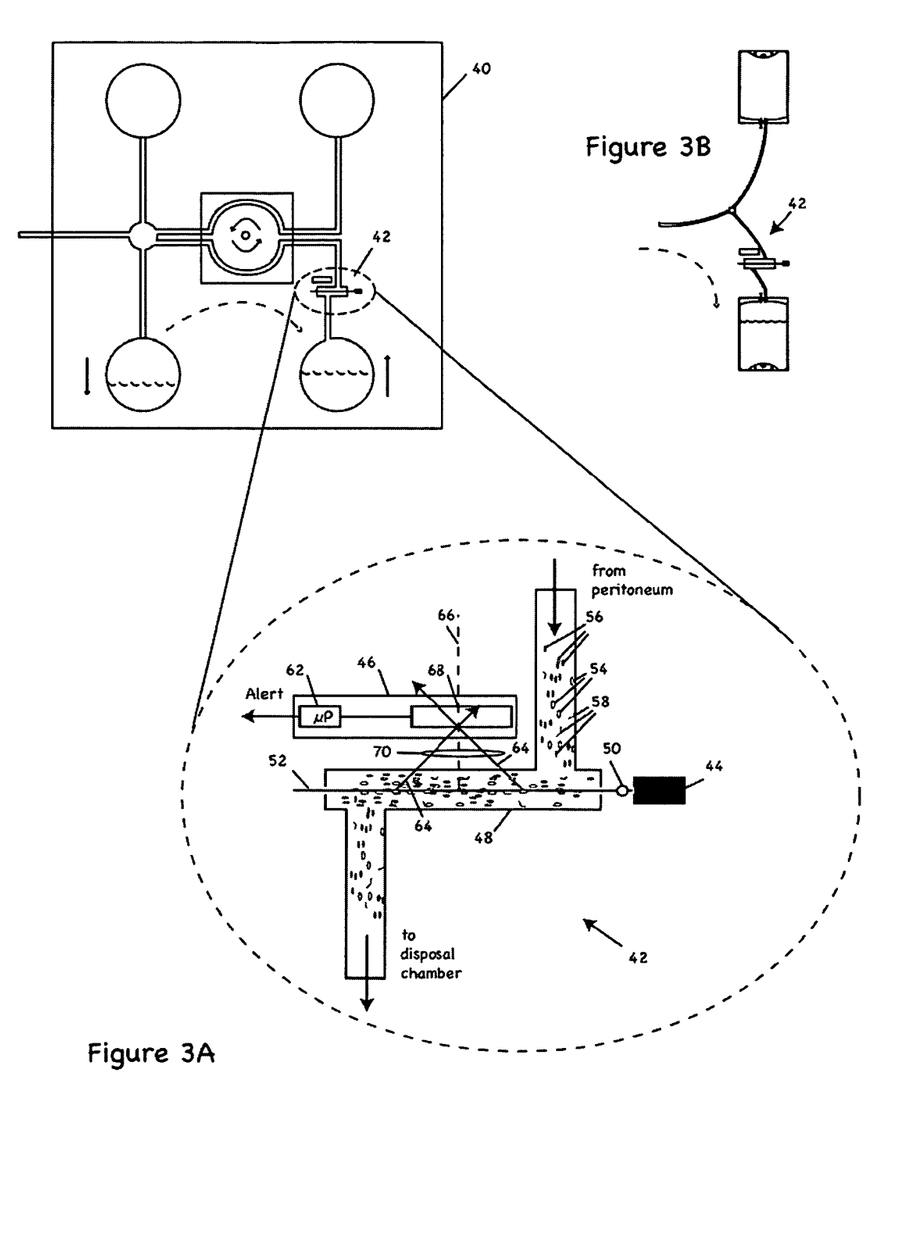
FIGS. 3A-3B depict apparatus for testing PD effluent according to one practice of the invention.

FIG. 3A depicts an APD cycler 40 that is constructed and operated in the manner of cycler 12 (FIG. 1), albeit including apparatus 42 according to the invention for testing PD effluent (i.e., PD solution drained from the peritoneum) in a flow path of cycler 40 and/or other APD system or components of which it is a part. The cycler 40 (with test apparatus 42) can be used in place of cycler 12 in the system 10 (FIG. 1), as well as in other APD treatment systems. Likewise, the test apparatus 42 can be coupled into the effluent flow path (i.e., drain lines) of the system 30 (FIG. 2), as graphically depicted in inset FIG. 3B, as well as in other CAPD systems. Moreover, the apparatus can be combined with kits for APD and CAPD procedures (e.g., kits that include tubing, clamps, sterilization wipes and so forth). Still further, the apparatus 42 can be coupled into fluid flow paths of laboratory, doctor's office, hospital or home test equipment and it can be sold with kits for such testing (e.g., kits that include PD effluent sample phials, drop boxes, labeling and so forth). For convenience, operation of test apparatus 42 will be described with respect to cycler 40 of FIG. 3A, though, it will be appreciated that apparatus 42 can be configured and operated similarly in the aforementioned and other environments in which it is used.

By way of overview, illustrated apparatus 42 tests PD effluent in a flow path—here, the path from peritoneum 14 to disposal chamber 24—for the onset of peritonitis and/or other conditions (e.g., the presence of blood and/or bubbles). To this end, that apparatus includes an illumination source 44 and a detector 46. The source 44 is arranged to illuminate peritoneal effluent in a chamber 48 that forms part of the flow path, and the detector 46 is arranged to detect illuminant scattered by that effluent, e.g., in a direction normal to the illuminant beam.

The source 44 and detector 46 are configured so that the detector detects reflected and/or scattered (collectively, "scattered") illuminant at a cellular scale of resolution, e.g., on a scale such that separate cellular-sized biological (or other) components in the effluent can be distinguished from one another. In applications such as those to which the illustrated embodiment is directed, i.e., early detection of the onset of peritonitis, this permits separate white blood cells (WBCs) in the effluent to be distinguished from one another (as well as from red blood cells, fibrin and other components of the effluent) so that they can be counted and so that the rate of change of those counts can be measured for purposes of detecting and signaling the onset of peritonitis. In other embodiments, this permits red blood cells (or other components, such as bubbles) in the effluent to be distinguished from one another (as well as from WBCs, fibrin, etc.) and counted; and so forth.

As noted, detector 46 is configured to detect illuminant scattered from the chamber 48 at a cellular scale of resolution, e.g., on a scale such that separate cellular-sized components in the effluent can be distinguished from one another. As further noted, in the illustrated embodiment, this permits separate WBCs 54 in the effluent to be distinguished from one another (as well as from red blood cells 56, fibrin 58 and other components of the effluent) so that they can be counted and so that the rate of change of those counts can be measured for purposes of detecting and signaling the onset of peritonitis. In other embodiments, this permits other components—such as RBCs 56, fibrin 58, etc.- to be detected in the effluent for purposes signaling other other conditions.

The illumination source of the illustrated embodiment comprises a low-power laser diode generating a monochromatic collimated beam. Here, the wavelength is selected at 630 nm to coincide with an optical sensitivity of detector 46 and for suitability in reflection and scattering (collectively, as above, "scattering") from at least selected components (e.g., white blood cells) in the effluent. Other embodiments may utilize lasers of other wavelengths, monochromatic or otherwise, selected in accord with foregoing or other criterion, e.g., 830 nm and 780 nm lasers, to name but a few, as well as other illumination sources, monochromatic, polychromatic, coherent and/or otherwise.

The collimated beam generated by laser diode 44 of the illustrated embodiment is optionally shaped by lens or columinator 50 to result in a beam 52 of gaussian or circular cross-section, though beams of other shapes may be used in other embodiments.

Lens 52 shapes the beam to optimize scattering from at least selected components in the effluent. In the illustrated embodiment, this means sizing the beam at 1×-2× and, preferably, about 1.5× the average size of the effluent components to be preferentially be detected—here, WBCs. Given an average size of 12-15 µm for neutrophils and eosinophils, 8-10 µm for lymphocytes, and 16-20 µm for monocytes, beam 52 of the illustrated embodiment is accordingly sized between 10-40 µm and, preferably, 15-25 µm and, still more preferably, about 20 µm. This optimizes the apparatus 42 for preferential detection of WBCs over, for example, red blood cells 56, fibrin 58 and other components of the PD effluent. Other embodiments may use other beam sizes, e.g., for reason of preferential detection of other effluent components or otherwise.

The beam 52 of the illustrated embodiment is aimed to pass through chamber 48 in order to illuminate the effluent therein for purposes of evoking scattering from biological (and other) components in that fluid. Although in the illustrated embodiment, the beam is aimed to pass through a center of the chamber 48, as shown, in other embodiments the beam 52 may be directed otherwise.

Turning back to FIG. 3A, detector 46 detects and counts scattering events—i.e., events in which illuminant is scattered from the effluent in the chamber 48 to the detector 46—based on the intensity and/or location of those events. In the illustrated embodiment, the detector 46 is, particularly, arranged to detect side-scattering, e.g., events within a field of view 64 centered on an axis 66 that is normal to the beam 52, as shown. In other embodiments, the detector may be arranged to detect other scattering events, e.g., back-scattering, forward-scattering, side-scattering at angles β other than normal. Thus, while in the illustrated embodiment, β is substantially 90°, more generally, β is in the range 30°-150°; more preferably, between, 60°-120°; still more preferably, between 80°-100°; and, still more preferably, substantially 90°, as illustrated.

In some embodiments, the detector 46 employs a single-cell (or few-celled) photo diode, i.e., pin-diode 68, for purposes of detecting and signaling the occurrence of such scattering events. A lens 70 facilitates focusing the diode so that it detects those events at a cellular scale of resolution, e.g., on a scale such that separate cellular-sized biological (or other) components in the effluent can be distinguished (based on such scattering) from one another. In the illustrated embodiment, lens 70 is selected and arranged (vis-a-vis chamber 48 and diode 68) to preferentially focus WBCs, though, in other embodiments, the lens 70 may be focused otherwise. The lens 70 is further selected and arranged for a desired depth of focus within the field of view 64, e.g., in the illustrated embodiment, a depth of focus matching the depth of compartment 48, or a substantial portion thereof. The chamber 48 is configured to match the laser beam size and shape, e.g., so as to minimize or wholly avoid reflections (or scattering) of the beam 52 off the inner walls of the chamber itself The laser diode 68 is selected and/or otherwise configured (e.g., through use of appropriate circuitry) to detect scattering from selected components of the effluent—here, preferentially, WBCs, though, in other embodiments, RBCs, fibrin, bubbles other components of the effluent. Regardless, such selection and/or configuration can be performed empirically (e.g., by testing scattering detected from an effluent of known composition) or otherwise.

Scattering events detected and signaled by the diode 60 are routed to a microprocessor 62 (or other suitable element) for analysis. In the illustrated embodiment, this comprises counting events signaled over time and generating an alert, e.g., when the number of counts of a certain intensity (or range of intensities) varies, e.g., (i) from a baseline established for patient 16, (ii) among successive drains of spent PD solution from that patient 16, and/or (iii) when a trend of that variance over time—and, more particularly, a rate of change of counts over time (i.e., a "critical slope")—exceeds a selected amount. Such an alert can be in the form of a visible and/or audible signal to the patient 16, health-care worker, or otherwise; a hardware or other interrupt to system 12 of which test apparatus 42 forms a part; a software function call to such system; or otherwise.

Other embodiments of the invention employ a charge-coupled device (CCD), in place of pin-diode 68, for purposes of detecting and signaling the occurrence of scattering events. As above, lens 70 facilitates focusing the CCD (and obtaining a desired depth of focus) so that it detects those events at a cellular scale of resolution and, in the illustrated embodiment, so that it preferentially focuses WBCs—though, in other embodiments, the lens 70 may be focused otherwise. In the discussion that follows, elemental designation 68 is used for the CCD, as it was for the pin-diode, since the CCD is disposed in the same functional place in apparatus 42.

As with the pin-diode, the CCD 68 is selected and/or otherwise configured to facilitate detection of scattering from selected components of the effluent (again, here, preferentially, WBCs). In this regard, the CCD 68 images the illuminated chamber 48, recording both the positions and intensities of scattering events (again, at a cellular scale of resolution) so that at least selected components (e.g., WBCs) in the effluent can be distinguished from one another and from other components of the effluent.

Figure 4:
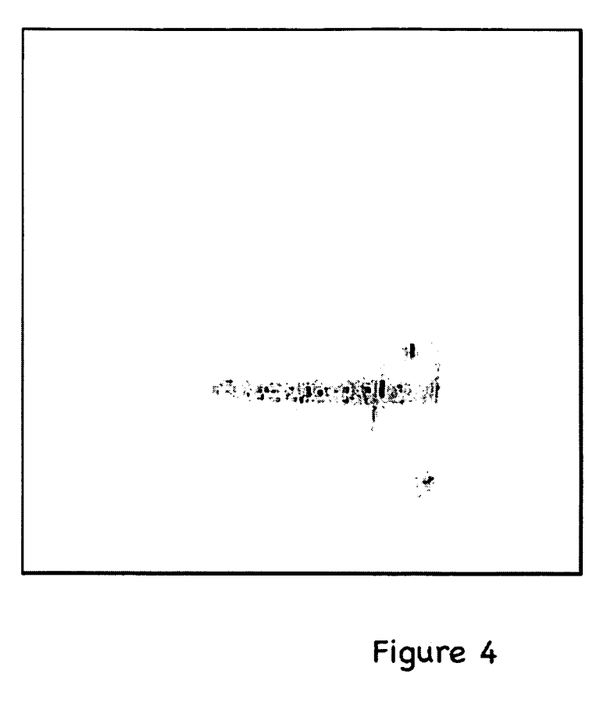
FIG. 4 depicts an image of the type generated by a charge coupled device in an apparatus according to one practice of the invention.

FIG. 4 depicts such an image—here, generated from a simulated effluent incorporating, in lieu of WBCs, 80 glass beads (sized between 10-30 microns) per μL.

Images generated by the CCD are routed to the microprocessor 62 (or other suitable element) for analysis. In the illustrated embodiment, this comprises taking a histogram of each image—or, more preferably, from multiple such images generated during drainage of spent PD solution following a single PD treatment session—with binning that is based on intensity. Depending on the number of counts in selected one(s) of the histogram bins, the microprocessor 62 can generate an alert, e.g., as discussed below.

Figure 5A:
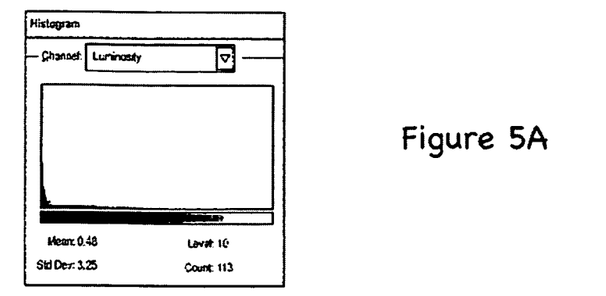
FIGS. 5A-5C depict histograms of the type generated from images generated by charge coupled devices used in practice of the invention.
Figure 5B:
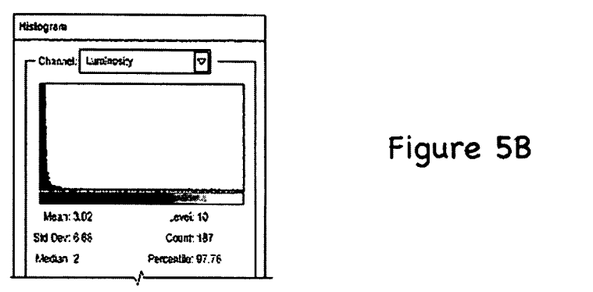
Figure 5C:
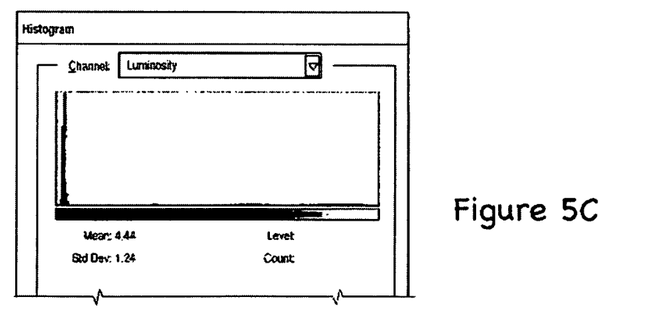

FIGS. 5A-5C depict such histograms—here, generated from a simulated effluent as described above with, respectively, 40 (FIG. 5A), 80 (FIG. 5B) and zero (FIG. 5C), glass beads per μL.

In the illustrated embodiment, it generates that alert, e.g., when the number of counts of a certain intensity (or range of intensities) varies, e.g., (i) from a baseline established for patient 16, (ii) among successive drains of spent PD solution from that patient 16, and/or (iii) when a trend of that variance over time (i.e., from PD treatment session to session)—and, more particularly, a rate of change of counts over time (or "critical slope")—exceeds a selected amount. Again, such an alert can be in the form of a visible and/or audible signal to the patient 16, health-care worker, or otherwise; a hardware or other interrupt to system 12 of which test apparatus 42 forms a part; a software function call to such system; or otherwise.

As will be appreciated, an advantage of taking histograms from multiple CCD images is that it tends to emphasize intensity counts in the critical range. This improves the signal-to-noise ratio and, thereby, increases the efficacy of detection (e.g., of peritonitis or other conditions reflected by the effluent). In embodiments of the invention using this approach, the CCD 68 can be controlled (e.g., by the microprocessor 62 or otherwise) to acquire those multiple images during PD solution drainage by successively entering "acquisition" and "read" modes: the former, for acquiring images of the illuminated chamber 48; and the latter for reading those images to the microprocessor.

In other embodiments of the invention, the microprocessor can perform image pre-processing prior to taking the histograms. Thus, for example, it can eliminate pixel values representing scattering from effluent components that are too long (e.g., fibrin) or too short (e.g., RBCs)—both, by way of example, with respect to embodiments intended to count WBCs for purposes of peritonitis detection. Further such preprocessing may be selected depending upon the specifics of the application to which the invention is applied.

Self-Cleaning Chamber

Figure 6A:
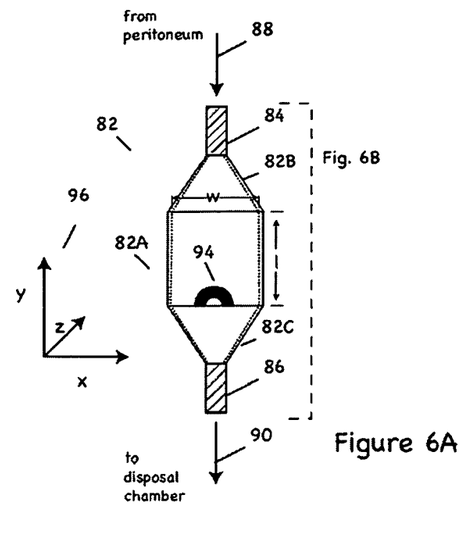
FIGS. 6A-6C show an alternate effluent flow chamber for use in a system according to the invention.
Figure 6B:
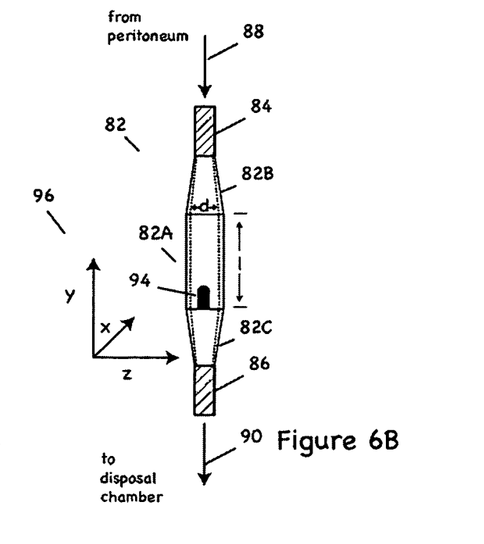
Figure 6C:
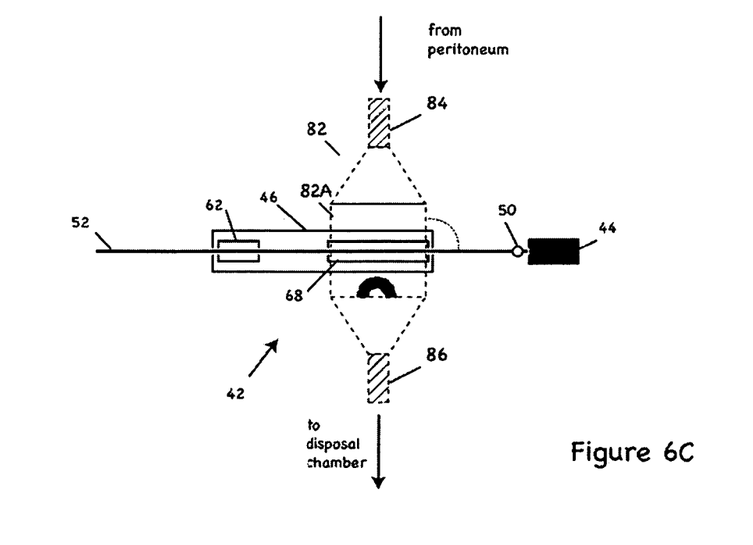

FIGS. 6A-6C depict a chamber 82 for use with apparatus 42. This is an alternate to the chamber 48 shown in FIG. 3A and discussed above. Thus, as with chamber 48, chamber 82 forms part of the flow path for peritoneal effluent and can be arranged so that effluent flowing through it can be illuminated by source 44 and detected by detector 46, all as described above with respect to chamber 48 in view of the discussion below.

FIGS. 6A and 6B depict front and side views, respectively, of chamber 82. FIG. 6C illustrates a configuration of a system according to invention showing chamber 82 in combination with source 44 and detector 46.

Referring to FIGS. 6A and 6B, chamber 82 includes a fluid inlet port 84 and outlet port 86 for coupling into the effluent flow path of cycler 40, system 30, or other APD or CAPD systems as described above, with effluent fluid flow in the direction of arrows 88, 90 from the peritoneum (or "transfer side") to the disposal chamber ("or drain side"). In the illustrated embodiment, the ports 84, 86 are dimensioned for attachment of tubing otherwise defining such effluent flow path in such APD or CAPD systems; though, it will be appreciated that the sizing and configuration of the ports may vary in other embodiments.

Chamber 82 defines a region in which effluent flowing in port 84 passes prior to exit via port 86. The chamber 82 of the illustrated embodiment includes a central portion 82A with inner walls (indicated by dashed lines) defining a fluid flow region generally characterized as a rectangular parallelepiped, or cuboid, with dimensions l (length), w (width), and d (depth).

In the illustrated embodiment, the length l and width w are generally of the same size, and both are greater in size than the depth d; however, other embodiments may vary in these regards. In one embodiment of the invention, l and w are both less than or equal to about 5" and, preferably, less than or equal to about 3" and, still more preferably, less than or equal to about 1", while d is less than or equal to about 1" and, more preferably, less than or equal to about ½" and, still more preferably, less than or equal to about ¼". Thus, in one particular embodiment, l and w are about 1" and d is about ¼".

The central portion 82A is coupled with port 84, on the inlet side, via a proximal portion 82B having inner walls (dashed lines) with a shape generally characterized as a pyramidal frustum; and, on the outlet side, via distal portion 82C having inner walls (dashed lines) also with a shape generally characterized as a pyramidal frustum. The dimensions of the frustum defined by the inner walls of portion 82B at the proximal end (i.e., closer to the inlet) substantially match the inner diameter of the port 84 and, at the distal end (i.e., close to the outlet), substantially match the dimensions of cuboid defined by the inner diameter of portion 82A. Likewise, the dimensions of the frustum defined by the inner walls of portion 82C at the distal end (i.e., closer to the outlet) substantially match the inner diameter of the port 86 and, at the proximal end (i.e., close to the inlet), substantially match the dimensions of cuboid defined by the inner diameter of portion 82A.

Central portion 82A of the illustrated embodiment is optically clear, permitting illumination of peritoneal effluent in chamber 82 by source 44 and detection of illuminant scattered thereby by detector 46, as discussed above. To these ends, at least central portion 82A can be fabricated from molded plastics such as acrylic, polycarbonate and/or polystyrene, which have optical transmission of 450 nm-890 nm (with maximum optical loss of around three percent) and are therefore suitable for use with a source 44 operating at a wavelength of 630 nm (+/−20 nm). Of course, other plastics or materials (such as glass, ceramics, etc.) that are optically transparent in the wavelengths discussed herein and earlier may be used as well or in addition.

In the illustrated embodiment, the index of refraction of the plastic or other material from which central portion 82A is fabricated (within the constraints discussed above) has little significant impact on illumination of peritoneal effluent in chamber 82 by source 44 and detection of illuminant scattered thereby by detector 46. However, in other embodiments, e.g., where a portion of region 82A serves as a lens (intentionally or otherwise), the index of refection of that plastic or other material may be more significant.

Likewise, in the illustrated embodiment, the dispersion factor of the plastic or other material from which central portion 82A is fabricated (again, within the constraints discussed above) has little significant impact on illumination of peritoneal effluent in chamber 82 by source 44 and detection of illuminant scattered thereby by detector 46. This is particularly true where (i) the beam 52 transits the walls of central portion 82 at an angle $\Omega$ that is substantially normal to the surfaces thereof, (ii) the beam is collimated, and (iii) the beam has a diameter (and is positioned) so that no portion of it comes in contact with the sides of the central portion 82A—other than the points of transit. However, in other embodiments, where the beam transits the walls of the central at an angle $\Omega$ other than substantially 90° central portion 82A can be fabricated from materials with lesser dispersion factors.

Although portions 82B, 82C of compartment 82 can be fabricated from the same plastic or other material as portion 82A, proximal and distal portions 82B, 82C need not be optically clear and, hence, can be fabricated from other materials, as well.

A deflector 94 is disposed at the distal end of the interior chamber 82, as shown. In the illustrated embodiment, it comprises an arc- or hemispherically-shaped member positioned in a central region of the effluent flow path downstream of a region illuminated by beam 52. Thus, for example, the deflector may be disposed at the distal end of chamber 82, yet, substantially centered vis-a-vis the x- and z-axes 96 (or, put another way, vis-a-vis the width w and depth d dimensions).

The deflector 94, which may be coupled or integral to the distal portion 82, has a rounded portion (shown as a thick, dark, curved region in the drawing) that protrudes into the distal end of the central portion 82A, as shown. Deflectors of other shapes suitable for breaking up the effluent flow (e.g., from lamellar to turbulent) in the manner discussed below may be used, as well or in addition to deflector 94 shown here. Deflector 84 may be fabricated from the same plastic or other materials as portions 82A, 82B and/or 82C, though it may be fabricated from other materials as well. In some embodiments, deflector 84 bears a coating of teflon or other substance that resists adherence of biological and other materials in the effluent flow.

As a consequence of the configuration of its inner walls, chamber 82 induces lamellar flow in effluent at the proximal end of the central portion 82A. The deflector 94 provides a transition in that flow at the distal end of the central portion 82A, as well as in outlet (or distal) portion 82C, from lamellar to turbulent by breaking up the boundary layer, which causes the Reynold's Number to increase. When the Reynold's number reaches 100, eddies start to form in the effluent. Those eddies increase as the Reynold's number gets larger. The eddies help clean the inner walls of the chamber 82—particularly, for example, at the distal end of the central portion 82A, as well as in distal portion 82C—preventing white blood cells, red blood cells, and other components of the effluent from adhering to those inner walls and/or removing those that have already adhered. Thus, in one embodiment of the invention, the deflector is arranged to effect a flow of effluent having a Reynold's Number that is about 100 or higher and, more preferably, about 250 or higher.

In Vivo Testing

Figures 7A, 7B:
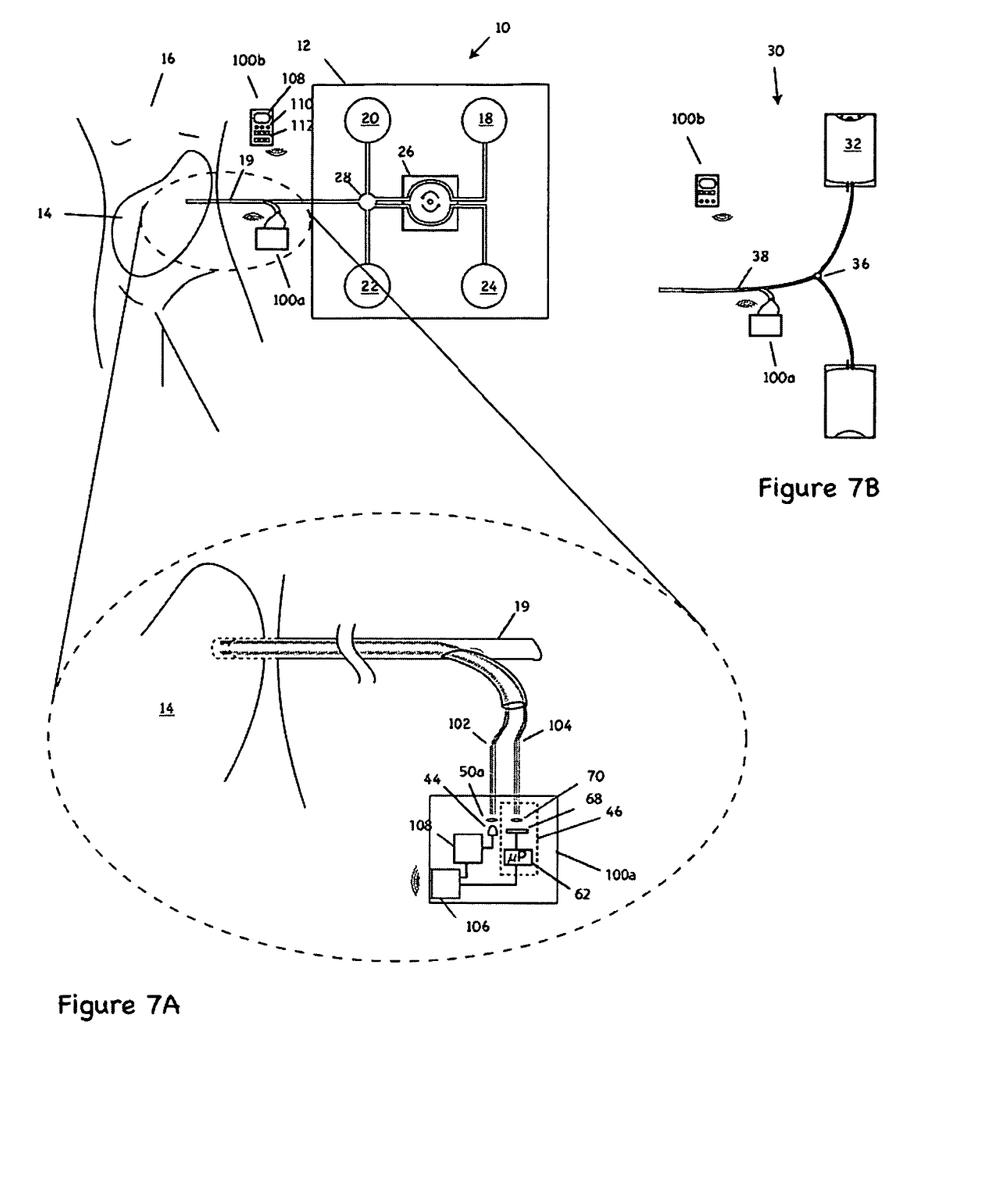
FIGS. 7A-7B depict APD and CAPD systems according to the invention utilizing apparatus for in vivo testing of peritoneal fluid according to the invention.

FIG. 7A depicts an APD cycler 40 that is constructed and operated in the manner of cycler 12 (FIG. 1), albeit including apparatus 100a according to the invention for detection of peritonitis by testing peritoneal fluid in vivo, i.e., in the patient's peritoneum. The cycler 40 (with test apparatus 100a) can be used in place of cycler 12 in the system 10 (FIG. 1), as well as in other APD treatment systems. Likewise, the test apparatus 100a can be used with system 30 (FIG. 2), as graphically depicted in inset FIG. 7B, as well as in other CAPD systems. Moreover, the apparatus 100a can be utilized as a stand-alone test apparatus (e.g., for testing fluids in a patient's body) and/or it can be combined with kits for APD, CAPD or other medical procedures. Still further, the apparatus 100a can be used, alone or in combination with the foregoing, in laboratory, doctor's office, hospital or home test equipment. For convenience, operation of test apparatus 100a will be described with respect to cycler 40 of FIG. 3A, though, it will be appreciated that apparatus 100a can be configured and operated similarly in the aforementioned and other environments in which it is used.

Illustrated apparatus 100a generally operates in the manner of test apparatus 42, discussed above, albeit testing peritoneal fluid in vivo for the onset of peritonitis and/or other conditions (e.g., the presence of blood and/or bubbles)—in the abdomen and, more particularly, in the peritoneum 14 of the patient 16—rather than in chamber 48. In addition, apparatus 100a of the illustrated embodiment provides for measurement of characteristics of the peritoneal fluid, e.g., its index of refraction.

When used with APD and CAPD systems (e.g., as shown in FIGS. 7A-7B), this testing is typically conducted during PD treatment—i.e., at a time when the peritoneum is filled with a mix of bodily fluids (e.g., creatin and urea) and PD solution. The apparatus 100a may also be used pre- or post-treatment to test peritoneal fluid that comprises substantially only bodily fluids. In light of the latter, it will be appreciated that the term "peritoneal fluid" as used herein in regard to the content of the peritoneum refers to any combination of fluids (e.g., bodily fluids, PD solution, or a mix thereof), unless otherwise evident from context.

To these ends, apparatus 100a utilizes a first fiber optic bundle 102 to carry illuminant down catheter 19 from illumination source 44 (external to the patient) into the peritoneum 14. A second fiber optic bundle 104 carries illuminant scattered by peritoneal fluid in the peritoneum, e.g., in a direction normal to the illuminant beam, back up the catheter 19 to the detector 46 (also external to the patient). In embodiments where apparatus 100a is used with APD and CAPD systems, the bundles may be routed through transfer sets 38, as well.

Figure 8:
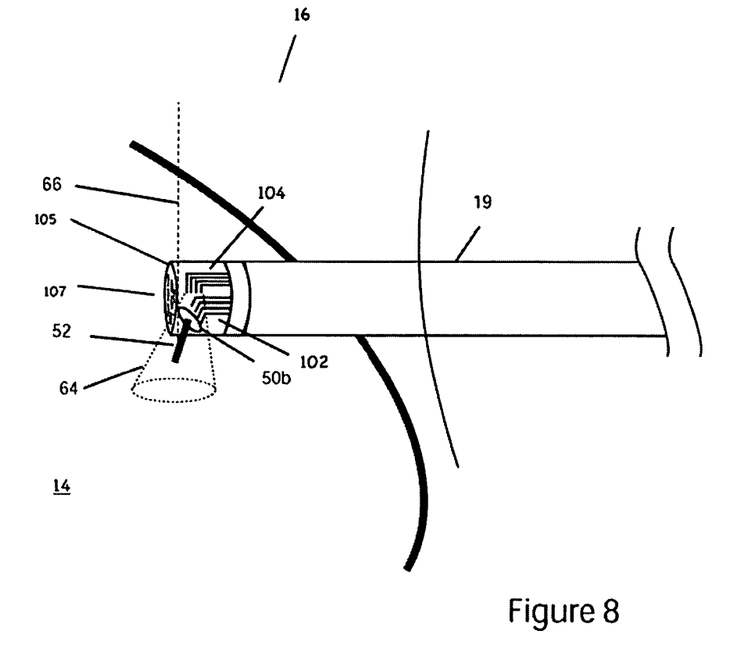
FIG. 8 depicts further details of the in vivo testing apparatus of FIG. 7.

Referring to FIG. 8, the distal ends of bundle 102 and bundle 104 are secured in catheter tip 105 so that the latter captures and transmits to detector 46 reflected and/or scattered (collectively, "scattered") illuminant—preferably, at a cellular scale of resolution, e.g., on a scale such that separate cellular-sized biological (or other) components in the peritoneal fluid can be distinguished from one another. As noted above, in applications such as those to which the illustrated embodiment is directed, i.e., early detection of the onset of peritonitis, this permits separate white blood cells (WBCs) in the peritoneal fluid to be distinguished from one another (as well as from red blood cells, fibrin and other components of the fluid) so that they can be counted and so that the rate of change of those counts can be measured for purposes of detecting and signaling the onset of peritonitis. In other embodiments, this permits red blood cells (or other components, such as bubbles) in the fluid to be distinguished from one another (as well as from WBCs, fibrin, etc.) and counted, and so forth.

Tip 105 may be constructed of plastic, ceramic, metal or other materials (or combination thereof) suitable for use in medical application for securing the bundles 102, 104. In the illustrated embodiment, it comprises a hood-shaped structure with a hollow central region in which the distal ends of bundles 102, 104 are disposed (as shown) and through which peritoneal fluids, as well as fresh and spent dialysate, may freely pass. An open "face" region of the hood-shaped structure and apertures 107 at its distal end (or "top") further facilitates such passage of fluids. In addition, the open face and apertures help insure that distal tips 102, 104 are exposed to a representative mix of fluids from the peritoneum. Those skilled in the art will of course appreciate that other structures and/or arrangements may be used in addition to, or in place of, tip 105.

Fiber optic bundles 102, 104 can be routed from apparatus 102 to peritoneum 14 through catheter 19 in the manner shown, e.g., entering the catheter 19 via an integral catheter branch 19a. Alternatively, the bundles 102, 104 can enter the catheter via a y-connector, via direct insertion into the wall of the catheter 19, or via other techniques known in the art for the routing of fiber optic bundles or other such structures through catheters into a patient's body. The bundles 102, 104 are comprised of conventional fiber optic fibers suitable for use in medical applications. Each bundle, which is sized to that it (and its partner) may pass through the catheter 19 without unduly impeding the flow of dialysate therethrough, comprise between one and hundreds, or more, of fibers, depending on individual fiber size.

As above, illumination source 44 of apparatus 100a comprises a low-power laser diode generating a monochromatic collimated beam. The wavelength is selected at 630 nm to coincide with an optical sensitivity of detector 46 and for suitability in reflection and scattering (collectively, as above, "scattering") from at least selected components (e.g., white blood cells) in the peritoneal fluid. As noted earlier, other embodiments may utilize lasers of other wavelengths, monochromatic or otherwise, selected in accord with foregoing or other criterion, e.g., 830 nm and 780 nm lasers, to name but a few, as well as other illumination sources, monochromatic, polychromatic, coherent and/or otherwise. Source 44 can be powered and otherwise driven by illustrated drive circuitry 108 in the conventional manner of laser diode drive circuitry known in the art—as adapted in accord with the teachings hereof.

As above, the collimated beam generated by laser diode 44 of apparatus 100a can be shaped by lens or columinator 50a for transfer down bundle 102 to the peritoneum 14. A further lens or columinator 50b can be provided at the distal end of the bundle 102 to shape the laser beam 52 in peritoneal cavity 14 in a gaussian or circular cross-section, though beams of other shapes may be used in other embodiments.

As above, lens 50b shapes the beam 52 to optimize scattering from at least selected components in the peritoneal fluid. In the illustrated embodiment, this means sizing the beam at 1×-2× and, preferably, about 1.5× the average size of the fluid components to be preferentially be detected—here, WBCs. Given an average size of 12-15 µm for neutrophils and cosinophils, 8-10 µm for lymphocytes, and 16-20 µm for monocytes, beam 52 of the illustrated embodiment is accordingly sized between 10-40 µm and, preferably, 15-25 µm and, still more preferably, about 20 µm. This optimizes the apparatus 42 for preferential detection of WBCs over, for example, red blood cells 56, fibrin 58 and other components of the peritoneal fluid. Other embodiments may use other beam sizes, e.g., for reason of preferential detection of other peritoneal fluid components or otherwise.

As above, the beam 52 emanating from the bundle 102 of the illustrated embodiment is aimed to pass through the peritoneum 14 in order to illuminate peritoneal fluid therein for purposes of evoking scattering from biological (and other) components in that fluid.

As above, illuminant scattered by peritoneal fluid in the peritoneum 14, e.g., in a direction normal to beam 52 is transmitted along the catheter 19 to the detector 46 by fiber optic bundle 104. From that illuminant, detector 46 determines the index of refraction of the peritoneal fluid, in addition to detecting and counting of scattering events (i.e., events in which illuminant is scattered by fluid in the peritoneum 14 to the distal end of bundle 104), based on the intensity and/or location of those events.

In the illustrated embodiment, the distal end of bundle 104 is arranged to capture (and transmit to the detector 46 for detection) side-scattering, e.g., events within a field of view 64 centered on an axis 66 that is normal to the beam 52, as shown. In other embodiments, the distal end of the bundle is arranged to capture (and transmit to the detector for detection) other scattering events, e.g., back-scattering, forward-scattering, side-scattering at angles β other than normal. Thus, while in the illustrated embodiment, β is substantially 90°, more generally, β is in the range 30°-150°; more preferably, between, 60°-120°; still more preferably, between 80°-100°; and, still more preferably, substantially 90°, as illustrated.

As above, in some embodiments, the detector 46 employs a single-cell (or few-celled) photo diode, i.e., pin-diode 68, for purposes of detecting and signaling the occurrence of such scattering events. A lens 70 facilitates focusing the diode so that it detects those events at a cellular scale of resolution, e.g., on a scale such that separate cellular-sized biological (or other) components in the peritoneal fluid can be distinguished (based on such scattering) from one another. In the illustrated embodiment, lens 70 is selected and arranged (vis-a-vis the proximal end of bundle 104 and diode 68) to preferentially focus WBCs, though, in other embodiments, the lens 70 may be focused otherwise. The lens 70 is further selected and arranged for a desired depth of focus vis-a-vis field of view 64, e.g., in the illustrated embodiment, a depth of focus from about a few centimeters to about a few inches.

As above, the laser diode 68 is selected and/or otherwise configured (e.g., through use of appropriate circuitry) to detect scattering from selected components of the peritoneal fluid—here, preferentially, WBCs, though, in other embodiments, RBCs, fibrin, bubbles other components of the fluid. Regardless, such selection and/or configuration can be performed empirically (e.g., by testing scattering detected from a fluid of known composition) or otherwise.

As above, other embodiments of the invention employ a charge-coupled device (CCD), in place of pin-diode 68, for purposes of detecting and signaling the occurrence of scattering events. And, too, lens 70 facilitates focusing the CCD (and obtaining a desired depth of focus) so that it detects those events at a cellular scale of resolution and, in the illustrated embodiment, so that it preferentially focuses WBCs—though, in other embodiments, the lens 70 may be focused otherwise. In the discussion that follows, elemental designation 68 is used for the CCD, as it was for the pin-diode, since the CCD is disposed in the same functional place in apparatus 100*a*.

As with the pin-diode, the CCD 68 is selected and/or otherwise configured to facilitate detection of scattering from selected components of the peritoneal fluid (again, here, preferentially, WBCs) and for determination of the index of refraction of the peritoneal fluid. In this regard, the CCD 68 images the illuminated peritoneal fluid (via fiber optic bundle 104), recording both the positions and intensities of scattering events (again, at a cellular scale of resolution) so that at least selected components (e.g., WBCs) in the peritoneal fluid can be distinguished from one another and from other components of that fluid.

As above, scattering events detected and signaled by the diode 60 are routed to microprocessor 62 (or other suitable element) for analysis. In the illustrated embodiment, this comprises counting events signaled over time and generating an alert, e.g., when the number of counts of a certain intensity (or range of intensities) varies, e.g., (i) from a baseline established for patient 16, (ii) among successive drains of spent PD solution from that patient 16, and/or (iii) when a trend of that variance over time—and, more particularly, a rate of change of counts over time (i.e., a "critical slope")—exceeds a selected amount. Such an alert can be in the form of a visible and/or audible signal to the patient 16, health-care worker, or otherwise; a hardware or other interrupt to system 12 of which test apparatus 100*a* forms a part; a software function call to such system; or otherwise. In addition, the microprocessor determines the index of refraction of the fluid in the peritoneum 14 based on the intensity of the scattering events detected by diode 60.

In the embodiment of FIGS. 7A-7B, such alerts and index of refraction measurements are transmitted from apparatus 100*b* to a remote interface unit 100*b*. Such transmission can be over a wireless or wired connection, or a combination thereof. In the illustrated embodiment, wireless transmission is employed via module 106, which utilizes the Bluetooth® wireless protocol to communicate (i.e., transmit and receive information) with remote unit 100*b*. Other embodiments may use infrared, 802.11, or other wireless communication technologies (including long-distance wireless technologies, like satellite) instead or in addition. Still others may utilize wired connections (such as USB cables, Ethernet, and so forth), in combination with or exclusive of such wireless technologies.

Apparatus 100*b*, which can be sized and configured to be slipped onto/into a pocket or "worn" by the patient 16, a health care provider, or otherwise, receives such alerts index of refraction measurements for display on LCD or other display screen 108 and/or LEDs or other indicators 110. To this end, the apparatus 100*b* can employ a microprocessor or other circuitry (not shown) for further analysis of the alerts and information from apparatus 100*a* regarding scattering events, index of refraction measurements and other information (e.g., regarding battery levels and/or other aspects of the operational status of apparatus 100*a*). Indeed, such a microprocessor or other circuitry resident in apparatus 100*b* can provide some or all of the functionality of microprocessor 62, thereby, reducing the circuitry requirements of apparatus 100*a*.

More generally, the microprocessor or other circuitry of resident in apparatus 100*b* can control apparatus 100*a*, e.g., activating detector 46 and/or drive circuitry 108. To this end, apparatus 100*b* provides a keyboard 112 for accepting input from the patient, health care provider or others for activating the unit, entering codes for pairing Bluetooth module 106 or otherwise coupling/decoupling apparatus 100*a* and 100*b* for communications, specifying operational modes for detector 46 and/or drive circuitry 108 (and, more generally, apparatus 100*a* and 100*b*), and/or otherwise.

The circuitry of apparatus 100*a* and 100*b* can be powered by batteries, such as by way of non-limiting example two flat "watch type" batteries (not shown), or otherwise. Furthermore, that circuitry can be implemented using surface mounted printed circuit board technology, or otherwise, in order to conserve space. As such, apparatus 100*a* of the illustrated embodiment is approximately 1.5"×1"×0.5", though, the dimensions of other embodiments may vary. Likewise, apparatus 100*b* of the illustrated embodiment is approximately 3"×2"×1", though, again, the dimensions of other embodiments may vary.

Described and shown herein are apparatus and methods for testing PD effluent meeting the objects set forth above. It will be appreciated that the embodiments described here are merely examples of the invention and that other embodiments, incorporating changes therein, fall within the scope of the invention. Thus, by way of non-limiting example, it will be appreciated that the apparatus and methods as described above for use in detecting peritonitis from PD effluent flow can be applied in detecting characteristics of dialysate and other fluids contained in and/or from other bodily organs and cavities in vivo, in vitro and otherwise, including detecting such conditions as blood (RBCs), bubbles and other desirable or undesirable byproducts of CAPD, APD and so forth, all by way of non-limiting example. Further, it will be appreciated that such apparatus and methods can be applied in detecting bubbles and other byproducts of hemodialysis.

In view thereof, what we claim is:

1. An apparatus for testing peritoneal dialysis (PD) effluent in a flow path, comprising:
    A) a chamber defining at least part of the flow path for the peritoneal dialysis effluent,
    B) an illumination source that illuminates peritoneal effluent flowing through the chamber,
    C) a detector that detects illuminant any of reflected and scattered (collectively, "scattered") by the effluent flowing through the chamber,
    D) the chamber inducing lamellar flow in the effluent; and
    E) the chamber including a deflector disposed in the flow path, the deflector effecting a turbulent flow of fluid in the chamber that at least partially cleans inner walls thereof.

2. The apparatus of claim 1, wherein the deflector increases turbulence of effluent flowing in the chamber.

3. The apparatus of claim 1, wherein the deflector increases a Reynolds number of effluent flowing in the chamber.

4. The apparatus of claim 1, wherein the deflector prevents components of the effluent from adhering to the inner walls of the chamber and/or removes those that have already adhered to those walls.

5. The apparatus of claim 1, wherein the chamber comprises a first portion with inner walls defining a fluid flow region generally characterized as a rectangular parallelepiped.

6. The apparatus of claim 5, wherein the first portion of the chamber is coupled with a flow inlet port via a portion having inner walls with a shape generally characterized as a pyramidal frustum.

7. The apparatus of claim 6, wherein the first portion is coupled with a flow outlet port via a portion having inner walls with a shape generally characterized as a pyramidal frustum.

8. An apparatus for testing peritoneal dialysis (PD) effluent in a flow path, the apparatus comprising:
    A) a chamber defining at least part of a path of flow for the peritoneal dialysis effluent and inducing lamellar flow therein,
    B) an illumination source that illuminates peritoneal effluent flowing through the chamber,
    C) a detector that detects illuminant any of reflected and scattered (collectively, "scattered") by the effluent as it flows through the chamber,
    D) the detector detects that scattered illuminant at a cellular scale of resolution such that at least selected separate cellular-sized components in the effluent can be distinguished from one another based on the illuminant that is scattered therefrom and that is (i) detected by the detector and (ii) counted; and
    E) the chamber including a deflector disposed in the flow path, the deflector effecting a turbulent flow of fluid in the chamber that at least partially cleans inner walls thereof.

9. The apparatus according to claim 8, in which the detector is arranged to detect illuminant scattered from separate white blood cells (WBCs) in the effluent such that those WBCs can be distinguished from one another.

10. The apparatus according to claim 9, wherein the detector counts WBCs in the effluent based on illuminant scattered therefrom.

11. The apparatus according to claim 10, wherein the detector signals an onset of peritonitis if said counts change over time and/or vary from a baseline.

12. The apparatus according to claim 11, wherein said baseline is a baseline previously established for a patient from which the PD effluent is drained.

13. The apparatus according to claim 8, in which the detector is arranged to detect illuminant scattered from cellular-sized components of different types in the effluent such that those components can be distinguished from one another.

14. The apparatus according to claim 13, in which the detector is arranged to detect illuminant scattered from white blood cells (WBCs) in the effluent such that they can be distinguished from red blood cells (RBCs), fibrin and/or other components from which illuminant is scattered in the effluent.

15. A method for testing peritoneal dialysis (PD) effluent in a flow path, comprising:
    A) inducing lamellar flow in peritoneal effluent flowing through a chamber defining at least a portion of the flow path,
    B) illuminating the peritoneal effluent flowing through the chamber defining at least a portion of the flow path,
    C) detecting illuminant any of reflected and scattered (collectively, "scattered") by the effluent as it flows through the chamber; and
    D) effecting turbulence in at least a portion of the flow of effluent in the chamber so as to at least partially clean inner walls thereof.

16. The method of claim 15, comprising utilizing a deflector that is disposed in a flow path defined by the chamber to effect such turbulence.

17. The method of claim 16, comprising utilizing the turbulence to prevent components of the effluent from adhering to the inner walls of the chamber and/or remove those that have already adhered to those walls.

* * * * *